US006421565B1

(12) United States Patent
Hemmingsson

(10) Patent No.: US 6,421,565 B1
(45) Date of Patent: Jul. 16, 2002

(54) CARDIAC MONITORING DEVICE AND A RATE RESPONSIVE PACEMAKER SYSTEM

(75) Inventor: Tryggve Hemmingsson, Sollentuna (SE)

(73) Assignee: Pacesetter AB, Järfälla (SE)

( * ) Notice: Subject to any disclaimer, the term of this patent is extended or adjusted under 35 U.S.C. 154(b) by 0 days.

(21) Appl. No.: 09/485,353

(22) PCT Filed: Jul. 30, 1998

(86) PCT No.: PCT/SE98/01425
§ 371 (c)(1),
(2), (4) Date: Feb. 4, 2000

(87) PCT Pub. No.: WO99/07285
PCT Pub. Date: Feb. 18, 1999

(30) Foreign Application Priority Data

Aug. 6, 1997 (SE) ............................................. 9702876

(51) Int. Cl.⁷ ............................................. A61N 1/362
(52) U.S. Cl. ....................................................... 607/17
(58) Field of Search ................. 607/5–24; 600/510

(56) References Cited

U.S. PATENT DOCUMENTS

| 3,938,502 A | 2/1976 | Bom |
| 4,109,644 A | 8/1978 | Kojima |
| 5,139,020 A | * 8/1992 | Koestner et al. |
| 5,188,106 A | * 2/1993 | Nappholz et al. |
| 5,465,721 A | 11/1995 | Kishimoto et al. |

FOREIGN PATENT DOCUMENTS

EP  0 503 839  9/1992

OTHER PUBLICATIONS

"Continuous Stroke Volume and Cardiac Output from Intra--ventricular Dimensions Obtained with Impedance Catheter," Baan et al., Cardiovascular Research, vol. 15 (1981), pp. 328–334.

* cited by examiner

Primary Examiner—Scott M. Getzow
(74) Attorney, Agent, or Firm—Schiff Hardin & Waite

(57) ABSTRACT

An implantable cardiac monitoring device as an A-mode ultrasound probe which is adapted to be positioned in the right ventricle of a heart, and which emits an ultrasound signal which is reflected from one cardiac segment of the left ventricle of the heart, and the ultrasound probe receives the resulting echo signal. The delay between the emission of the ultrasound signal and the reception of the resulting echo is measured, and from this delay a position of the cardiac segment is determined. The position of this cardiac segment, at least one reflecting the signal, is related to cardiac performance, and thus the monitoring device determines, from the detected position of the cardiac segment, the cardiac performance.

18 Claims, 1 Drawing Sheet

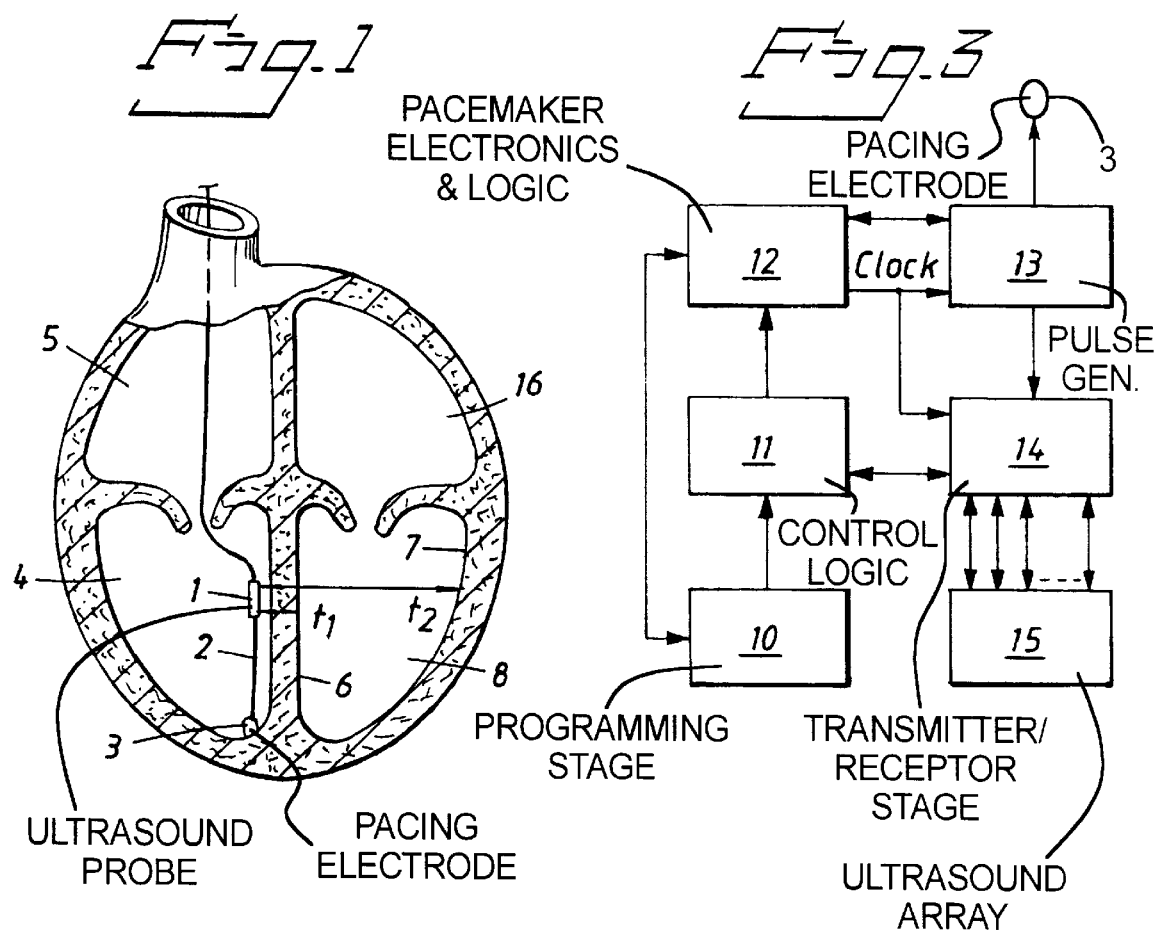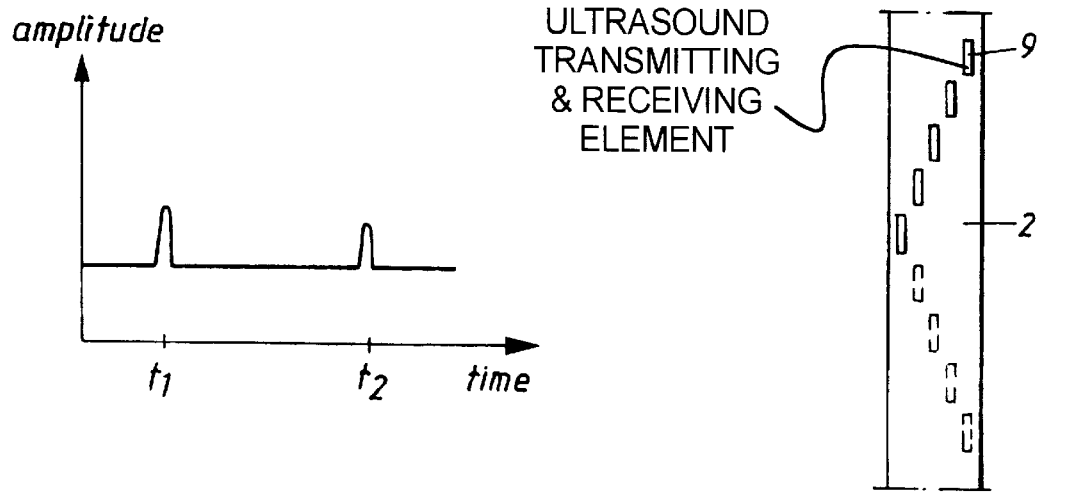

CARDIAC MONITORING DEVICE AND A RATE RESPONSIVE PACEMAKER SYSTEM

BACKGROUND OF THE INVENTION

1. Field of the Invention

The present invention relates to a cardiac monitoring device of the type having a component for transmitting a signal and receiving at least one echo of the signal reflected from at least one cardiac segment, a position of which, at least when reflecting the signal is related to the cardiac performance of a heart, and circuitry to determine a delay between the transmission of the signal and the receipt of the echo, and to derive from the delay the position of the cardiac segment.

The invention also relates to a rate responsive pacemaker system containing such a device.

2. Description of the Prior Art

Since a device of the above type is particularly suited for an application wherein it is arranged to register the position of a cardiac wall segment, it will, by way of example only, be described in relation to such an application hereinafter. Thereby, the cardiac performance refers to cardiac output and/or other parameters related to cardiac frequency, such as beat volume, cardiac contractility etc.

A device of the above type is described in U.S. Pat. No. 3,938,502, which describes a device for examining a hollow organ, such as a heart, having a catheter which is to be placed inside the hollow organ and which is provided at its end with circumferentially arranged, equidistantly distributed elements, each of which serves both for the transmission and reception of ultrasonic waves. In order to make it possible to completely visualize the moving cardiac structure, such as heart walls and heart valves, surrounding the catheter, at any moment, the device presents a large number of elements which show very little directivity in a plane perpendicular to the axis of the catheter, the elements being so dimensioned in the axial direction that the major part of acoustic energy in transmission is confined to a plane perpendicular to the axis of the catheter. Additionally, this known device includes an excitation unit which successively excites groups of adjacently arranged elements at a rate of at least 25 times per second. The transmitted and the received pulses for the elements of a group are respectively delayed so that the differences in travel times among the elements for the pulses to or from a line in the plane perpendicular to the catheter axis and being perpendicular to the center line of the group are compensated. This known device further includes an adder for the summation of the echo pulses brought into coincidence by the time delays. The known device is used for visually displaying the part of the examined hollow organ surrounding the catheter. This patent teaches the use of the equipment for direct imaging by means of a so called brightness mode (B-mode) ultrasound. The catheter described is primarily intended for examining a visualizing a heart, but is obviously not meant for implantation and would not possibly be used for such a purpose as it is considered highly energy consuming and would be of unacceptable size and weight for operation as an implantable equipment.

European Application 0 503 839 discloses a method and an apparatus for chronologically monitoring the hemodynamic state of a patient using Doppler ultrasound. Such a method and apparatus are used for regulating blood flow within the cardiovascular system in a closed-loop control system using ultrasound measurement techniques to determine a hemodynamic status of a patient and to derive a control parameter for modulating the hemodynamics of the system using electrical or pharmaceutical therapy. Heart contractility and the blood flow output from the heart is monitored in order to control an implantable cardiac assist or therapy device to maintain cardiac output without invading the left heart or the arterial system of the patient, Thus, the pacing rate of a cardiac pacemaker may be based on the determination of the cardiac output estimated by this device. The device is arranged to measure the cardiac output using Doppler ultrasound techniques in which a measuring transducer is implanted within the right heart and directed towards the left ventricle or aortic root. The transducer radiates acoustic energy at ultrasonic frequencies, then the device determines blood flow velocity by receiving and processing the resulting echo signals and measuring the shift in frequency of the returning echoes in comparison to the transmitted waves. The integral of the mean velocity curve is an accurate representation of stroke volume and cardiac output. However, the device is not provided to register the delay between the transmission of the signals and the receipt of the echoes thereof in order to derive from the delay a position of a certain cardiac segment. Moreover, the Doppler equipment to be used in the above application requires quite a lot of energy for its operation, and the output acoustic energy is likely to be too high to be used for permanent operation in a human body.

However, a device as disclosed in European Application 0 503 839 offers a possibility to register the hemodynamic situation in the systemic high pressure circulation of a heart, that is in the left atrium and left ventricle thereof, without needing to be located in said high pressure system. This is an advantage in comparison to prior pacemaker systems that are developed primarily to detect physiologic changes in the right atrium and/or right ventricle even though the action of the pulmonary or right side of the heart is only minimally representative of the hemodynamic situation in the high pressure part of the heart system, According to modern research and scientific publications as by Baan et at (Baan J. Jong I T. Kerkhof P L. Moene R i. van Dijk A D. van der Velde E I. Koops J. Continuos stroke volume and cardiac output from intra-ventricular dimensions obtained with impedance catheter. Cardiovascular Research 1981 June;15(6):328–34), a very good correlation exists between left ventricular diameter and cardiac output performance. The changes in intra-ventricular dimensions have been measured by means of electrical impedance. For this purpose, a catheter has been equipped with a number of electrodes spaced over a distance equal to the long axis of the left ventricle into which the catheter has been introduced. A constant current was imposed between the outermost electrodes while the inner ones were used to measure resistance of volume segments of the blood contained within the ventricular cavity. The difference in resistance at the beginning and the end of ejection was proportional to the contribution of each segment to stroke volume. The best correlation of left ventricular diameter to cardiac output performance was obtained when measuring in the middle of the axial length of the left ventricle.

SUMMARY OF THE INVENTION

An object of the present invention is to provide a cardiac monitoring device which permits to estimate the total cardiac performance of a heart, including the performance of the high pressure side of said heart, without interfering the function of the heart or being easily interfered by the function of the heart. Moreover, the device should be of a type that is implantable in mammals, and particularly human beings, and which permits to be used in such an application for a significant period of time. The device should also be of a type that requires a minimum of power consumption and is simple as to its construction.

The above object is achieved in accordance with the principles of the present invention in an implantable cardiac monitoring device having an A-mode ultrasound probe which is adapted to be positioned in the right ventricle at a heart, and which emits an ultrasound signal which is reflected from at least one cardiac segment of the left ventricle of the heart, the ultrasound probe receiving the resulting echo signal, and circuitry for determining a delay between the emission of the ultrasound signal and the reception of the resulting echo, and for determining, from this delay, a position of the cardiac segment, the position of this cardiac segment, at least when reflecting the signal, being related to cardiac performance, and the implantable cardiac monitoring device including a unit for deriving, from the detected position, the cardiac performance.

By directing the transmitted and correspondingly received signal or signals towards a cardiac segment the position of which correlates very well to the cardiac performance, that is the cardiac output performance, the device may be used to provide a pacemaker with information concerning that performance. Such information may then be used by the pacemaker system in order to suitably control the very pacing of the heart. The inventive device permits monitoring the condition of the left, high pressure side of the heart, while being positioned at another location, for instance in the pulmonary side of the heart.

As noted above, in a preferred embodiment of the device, the device is arranged to be positioned in at least one of the right atrium and right ventricle of a heart. Thereby, left atrial or ventricular movements and dimensions may be detected in a minimally invasive way while avoiding those problems that may appear if the device would be located in the left part of the heart, that is the left atrium or ventricle.

According to another preferred embodiment of the device, the ultrasound probe is arranged to direct the ultrasound signal toward the left ventricular wall of a heart, this wall defining the aforementioned cardiac segment. The echoes of the signal thus are received from the left ventricular wall and the position of the left ventricular wall at a certain movement during a cardiac cycle is correlated to the inner diameter of the left ventricle at that specific movement or, at least, to the volume of the left ventricle of the heart, the diameter or volume being correlated, in turn, to the cardiac output performance. Thus, by deriving the position of the left ventricular wall, a precise estimation of the momentary cardiac performance may be obtained.

According to another preferred embodiment of the device, the ultrasound probe is arranged to direct emitted ultrasound signal toward the medial portion and lateral portion of the endocardial wall of the left ventricle respectively, these portions defining the aforementioned cardiac segment, and the device includes circuitry which determines the echo delay difference between the echoes respectively reflected from these portions, and which, from this difference, determines the distance between these wall portions, this distance corresponding to the cardiac performance. Such an arrangement is particularly advantageous as it has been shown that the distance between these portions correlates very well with the cardiac output. In order to achieve this, the device is preferably arranged at a catheter or the like arranged to be inserted in or near the heart and anchored therein in quite a fixed position.

According to another preferred embodiment, the inventive device forms a part of a rate responsive pacemaker system and is arranged to provide said system with cardiac performance information. The pacing may be adapted to the cardiac performance in every single situation. For example, in a DDDR-mode, the atrium and the ventricle operate in synchrony. At high atrial rates this synchronous behavior may be inappropriate or harmful. The pacemaker, by means of the inventive device, detects when synchronous behavior is harmful by measuring the cardiac output. While an atrial rate causes an elevation in cardiac output, the pacemaker allows the ventricle to respond to the atrial rate. When further increases in atrial rate lead to a sustained degradation in cardiac output, the pacemaker no longer allows synchronous pacing. By measuring cardiac output, the pacemaker system is able to determine when ventricular activity should not follow natural atrial heart beats and is able to adjust to a suitable pacing mode. In addition, using an indication of cardiac output, the pacemaker system can determine whether the heart is successfully responding to a pacing stimulus of a particular amplitude and pulse duration.

The ultrasound probe emits ultrasound according to the A-mode principle, defining the emitted signal. Thereby, the power consumption is minimal due to the fact that the periodic measurement frequency may be low, for example twice per cardiac cycle or less, and that, ideally, transmission may be performed in one direction only.

In one embodiment of the device, the ultrasound probe is formed by at least one ultrasound crystal, arranged on a pacemaker electrode. By arranging the crystal on the electrode a very precise position of the crystal may be defined. For example, a tip at the end of the electrode is arranged to be anchored at the very bottom of the right ventricle, resulting in the electrode extending through the ventricle in a very well defined way, thereby making it possible to locate the crystal with good precision at a suitable location along the electrode.

In another embodiment of the device the ultrasound probe is formed by an array of ultrasound crystals, distributed around the periphery of a pacemaker electrode, each of the ultrasound crystals being arranged to individually transmit and receive ultrasound pulses in a co-ordinated manner. This arrangement is to assure optimal transmission and reception performance even at possible rotation of the pacemaker electrode at the time of implantation or later. By checking which crystal receives the most appropriate echo, transformation and receipt of the ultrasound signals may then be performed with that single crystal. There is always at least one crystal active with optimal measurement performance and directed in a correct direction, e.g. toward the site of the left ventricle where the wall movements correspond best to the volume changes thereof and are large enough to be easily detected. For example, the crystals of the array may be arranged to scan their detection area at predetermined or optional occasions and the device can include circuitry to survey the scanning results to identify the best measured echo performance in order to choose which crystal or crystals are to be used for transmission until the next scanning event. By only receiving echoes within a certain temporal window and studying the amplitudes of the echoes received by the respective crystal within said temporal windows, it is possible to determine which echo performance is the best and most suitable one for further measurement. Preferably, the device is connected to or contains a logic unit of a pacemaker system, said logic unit being arranged to treat the information from each individual crystal and to determine which echo performance is the best.

According to another version of the embodiment wherein the ultrasound probe has a single ultrasound crystal, the device has a circuit for triggering the emission of ultrasound by single crystal at desired moments of a cardiac cycle from sensed IEGM-information by a pacemaker electrode connected this circuit. Thereby, the device is able to trigger two consecutive transmissions at selected moments during one or two cardiac cycles, e.g. when the ventricular volume is supposed to be at or near its minimum and maximum respectively, in order to derive the positions of the aforementioned cardiac segment at these moments in order to estimate the respective volumes at those moments, corresponding to the cardiac performance. By performing the transmission and receipt at such moments a very good correlation between the position of the respective cardiac segment, for instance the left ventricular walls, and the cardiac output is obtained. Particularly, the difference between minimum and maximum inner diameters of the left ventricle has a good correlation to the cardiac output, said correlation being taken advantage of by this specific arrangement of the device.

Another object of the present invention is to provide a rate responsive pacemaker system capable of estimating the cardiac performance, that is a cardiac output, and to use this information as a parameter in order to control its pacing or other operation.

Such a rate responsive pacemaker system contains a monitoring device according to the invention as previously described.

BRIEF DESCRIPTION OF THE DRAWINGS

FIG. 1 is a schematic view, showing the inventive device positioned on a pacemaker electrode inside the right ventricle of a heart, FIG. 2 is a diagram showing amplitude versus time for pulse echoes from the ventricular walls according to FIG. 1.

FIG. 3 is a schematic block diagram of the rate responsive pacemaker system of the invention, and FIG. 4 is a detailed view, showing an array of ultrasound crystals arranged in a twisted manner or helically around the periphery of a pacemaker electrode.

DETAILED DESCRIPTION OF A PREFERRED EMBODIMENT

According to FIG. 1 a simple amplitude mode (A-mode) ultrasound probe 1 is mounted near the distal end of a pacemaker lead 2. A tip 3 (at which a pacing electrode may be present) of the lead 2 is anchored at or near the apex of the right ventricle 4 of a heart 5. The ultrasound probe 1 is arranged to detect the position of the medial portion 6 and lateral portion 7 of the endocardial wall of the left ventricle 8 respectively, these portions 6 and 7 defining a cardiac segment from which an echo of a signal emitted by the ultrasound probe 1 is received by the ultrasound probe 1.

The ultrasound probe 1 contains at least one element 9 for emitting a signal and receiving at least one echo of this signal reflected from at least one cardiac segment, here constituted by the medial and lateral portions 6 and 7 of the endocardium. The element 9 may be an ultrasound (piezoelectric) crystal, and the ultrasound probe 1 can contain an array of such elements 9, helically arranged around the periphery of the lead 2. As shown in FIG. 4, ten elements 9 are provided. Each of the ultrasound elements 9 is arranged to individually emit and receive ultrasound information, alone or simultaneously with other elements 9, in a co-ordinated manner by emission and reception of ultrasound pulses as shown in the diagram of FIG. 2. The ultrasound emission of the device 1 is triggered by means of a pacemaker system according to FIG. 3 at the desired moment in cardiac cycles obtained from sensed IEGM-information by the pacemaker lead 2. Thereby, each ultrasound element 9 is electronically connected to the pacemaker system. The connection between the ultrasound leads and a corresponding adapter (not shown) of a pacemaker housing is made via small connectors or via a data interface whichever is easier to develop and manufacture.

The ultrasound element or elements 9 is/are arranged at a distance from the tip 3 of the lead 2 so as to be located approximately at the middle of the right ventricle in the lengthwise direction thereof when the tip 3 is anchored, preferably at or near the apex of the ventricle.

The element or elements 9 is/are arranged to emit ultrasound with an adjustable frequency of approximately 4–15 megahertz for optimal echo reception at a distance of approximately 3–15 cm. The emitted ultrasound pulses are about 1 millisecond wide and of an amplitude that is selected according to minimal detection level and distance requirement. The reception of the ultrasound pulses or signals is made according to a programmable calculated temporal window in such a manner that the corresponding ultrasound echo is received from a distance corresponding to the endocardial wall portions 6, 7 of the left ventricle. Accordingly, by using such a temporal window, it is possible to avoid receiving a disturbing echo from the adjacent medial endocardial wall of the right ventricle 4 when the device is located as in FIG. 1. The time delay t of reflected echo pulses from an impedance altering interface of e.g. heart tissue is equal to $2\times L/V$, where L is the distance from the element 9 to the reflecting tissue detected and V is the ultrasound velocity in the heart tissue.

Furthermore, the inventive device is connected to and forms a part of a rate responsive pacemaker system, schematically represented in FIG. 3 by means of a block diagram. This pacemaker system containing a programming stage 10, arranged to be programmed by means of a separate programmer (not shown) in a known manner.

The pacemaker system also contains control logic 11, pacemaker electronics and logic 12, a pulse generator 13 and a transmitter/receptor stage 14. The transmitter/receptor stage 14 is adapted to communicate with the ultrasound probe 1, here represented by an ultrasound crystal array 15. The pulse generator 13 is arranged to communicate with the pacemaker electronics and logic 12 and to receive therefrom a clock frequency. The pulse generator 13 is also arranged to transmit pulses to the transmitter/receptor stage 14. Furthermore, the pacemaker electronics and logic 12 is arranged to transmit a clock frequency to the transmitter/receptor stage 14. The control logic 11, which receives control information from the programming stage 10, is arranged to control the pacemaker electronics and logic 12 as well as the transmitter/receptor stage 14 and to receive information therefrom concerning transmission of signals, reception of echoes thereof, delays and delay differences as defined above. Thereby, the pacemaker system is able to take advantage of this information and use it as parameters in order to better control the operation and particularly the pacing of said system.

According to the invention the device, such as via the control logic 11 and the transmitter/receptor stage 14, is arranged to trigger at least two consecutive emissions of ultrasound pulses with corresponding echo receptions in the systolic phase of the cardiac cycle, or the diastolic phase of the cardiac cycle, or in each of the systolic phase and the diastolic phase of the same cardiac cycle, or in a desired phase of the cardiac cycle with an optional time difference between the two consecutive transmissions, or in a desired phase of the cardiac cycle selected via separate sensing ability of the rate responsive pacemaker. Preferably, the device receives control information regarding how to perform these measurements in a known manner through a pacemaker system similar or identical to the one schematically represented in FIG. 3.

A physician may control the operational mode of the ultrasound probe 1 manually by telemetrical programming features or by using an automatic sensing algorithm built into the system. For example, the physician may program the programming stage of the system such that the ultrasound crystals of the array scan the detection area at predetermined occasions, for example once a week, in order to choose the best measured echo performance and which crystal or crystals to be used for transmission of the signals and reception of echoes thereof. Preferably, the control logic 11 is also arranged or programmed to treat the transmission and receipt information and to derive therefrom the position of the medial and lateral endocardial wall of the left ventricle of a heart and to derive therefrom the corresponding volume of the left ventricle at each measuring occasion. By measuring the end-diastolic volume EDV and the end-systolic volume ESV and subtracting these dimension data EDV-ESV a relative measure of the stroke volume SV of the left ventricle may be obtained. As the stroke volume is a parameter related to the cardiac output CO of the heart (CO=Heart rate×SV) the pacemaker system is preferably arranged to use these data in order to control its pacing rate. Particularly, the system may be arranged to inhibit further increase of the pacing rate as, during an increase of the pacing rate, the stroke volume reaches a certain level where further increase of the pacing rate only would result in an even smaller stroke volume and thus would not be a correct measure to increase the total cardiac output.

This method permitted by the inventive device gives an indirect measure of cardiac output (through diameter variations during a cardiac cycle), but as the most important information from a sensor for rate responsive pacing is used to correct earlier sampled information and preset the desired heart rate, the A-mode ultrasound detector gives appropriate information to fulfil this task. As this sensor information is collected directly from the left ventricle of the heart and not limited to the right ventricle as with the main part of the cardiac pacing sensor techniques, it gives the optimal information from the cardiovascular situation for hemodynamic rate adapted pacing.

Of course variations and modifications of the present invention will be apparent to those skilled in the art without departing from the scope of the invention.

For example the measurement logics could be refined in future applications to measure absolute cardiac volumes. Furthermore, the ultrasound probe 1 does not need to be positioned on a pacemaker lead provided with a ring or a tip electrode 3, but could as well be attached onto a separate lead or electrode adapted to be positioned inside or outside the very heart and not necessarily anchored in a cardiac wall. However, it has been found favorable to mount the ultrasound probe 1 on a pacemaker lead, the tip of which is arranged to be anchored at the apex of the right ventricle. Thereby, the distance from the very tip 3 to the ultrasound probe 1, or the emitting and receiving element 9 thereof, preferably should be such that the element 9 then would be located approximately opposite to the point of the left ventricle 8 where the contraction thereof is as clear and easy to detect as possible and corresponds to the volume change of the ventricle. Thereby, the distance from the tip 3 to the element 9 should be in the order of 2–6 cm for use in the heart of a full grown adult.

In the embodiment using an ultrasound array, the number of elements 9 in the array may be more or less than ten as shown. In order to obtain a better precision a substantially larger number might be used, e.g. thirty crystals uniformly distributed around the periphery of the electrode.

Preferably, the element 9, or the array thereof, may be displaceably arranged along the longitudinal axis of the electrode or lead, thereby admitting adjustment to different heart sizes or to the growing heart of a child equipped with the device, or the positioning of the device in the atrium or ventricle.

Preferably, the operation of the inventive device may be used in a closed loop-system.

Although modifications and changes may be suggested by those skilled in the art, it is the intention of the inventor to embody within the patent warranted hereon all changes and modifications as reasonably and properly come within the scope of his contribution to the art.

What is claimed is:

1. An implantable cardiac monitoring device comprising:
  an A-mode ultrasound probe adapted for implantation in a right ventricle of a heart, said ultrasound probe emitting an ultrasound signal and receiving at least one echo of said ultrasound signal from at least one cardiac segment of the left ventricle;
  a unit connected to said ultrasound probe for identifying a time difference between emission of said ultrasound signal and reception of said echo and, from said time difference, determining a position of said cardiac segment, said cardiac segment having a position which, at least when reflecting said ultrasound signal, is correlated to cardiac performance, and said unit deriving an indication of said cardiac performance from said position of said cardiac segment.

2. A device as claimed in claim 1 wherein said ultrasound probe is adapted for implantation in the ventricle to emit said ultrasound signals toward, and receive said echos from, a left ventricular wall comprising said cardiac segment.

3. A device as claimed in claim 1 wherein said ultrasound probe is adapted for implantation in the ventricle to emit said ultrasound signal toward, and to receive respective echoes from, a medial portion of an endocardial wall of a left ventricle and a lateral portion of the endocardial wall of the left ventricle, comprising said cardiac segment, and wherein said unit identifies a time difference between the respective echoes received from said medial portion and said lateral portion and uses said time difference to derive said information about said cardiac performance.

4. A device as claimed in claim 1 wherein said ultrasound probe comprises at least one ultrasound element mounted on an electrode lead.

5. A device as claimed in claim 1 wherein said ultrasound probe comprises a plurality of ultrasound elements, forming an array, distributed around a periphery of a pacemaker electrode lead.

6. A device as claimed in claim 5 further comprising control circuitry connected to said ultrasound elements in said array for controlling said ultrasound elements to respectively emit ultrasound signals and to receive echoes therefrom in a controlled sequence.

7. A device as claimed in claim 1 further comprising means for sensing cardiac activity and for obtaining an IEGM signal representing said cardiac activity, and further comprising a control circuit connected to said ultrasound probe for triggering emission of said ultrasound signal at a selected time in a cardiac cycle determined from said IEGM signal.

8. A device as claimed in claim 7 wherein said control circuitry triggers two consecutive emissions of ultrasound pulses comprising an ultrasound pulse at a time when a ventricular volume of the heart, based on said cardiac cycle, is expected to be at a minimum and an ultrasound pulse at a time in said cardiac cycle when said ventricular volume is expected to be a maximum, and wherein said unit determines the ventricular volume as said cardiac performance.

9. A device as claimed in claim 8 wherein said control circuitry triggers said two consecutive emissions during a single cardiac cycle.

10. A device as claimed in claim 8 wherein said control circuitry triggers said two consecutive emissions respectively in two successive cardiac cycles.

11. A device as claimed in claim 7 wherein said control circuitry triggers at least two consecutive emissions of ultrasound pulses in a systolic phase of said cardiac cycle.

12. A device as claimed in claim 7 wherein said control circuitry triggers at least two consecutive emissions of ultrasound pulses in a diastolic phase of said cardiac cycle.

13. A device as claimed in claim 7 wherein said control circuitry triggers two consecutive emissions of ultrasound pulses in each of a systolic phase of a single cardiac cycle.

14. A device as claimed in claim 7 wherein said control circuitry triggers two consecutive emissions of ultrasound pulses at a selected phase in said cardiac cycle with a selected time difference between said two consecutive emissions.

15. A device as claimed in claim 7 further comprising means for separately sensing a physiological parameter associated with cardiac activity, and wherein said control circuitry triggers two consecutive emissions of ultrasound pulses at a phase of said cardiac cycle selected dependent on said physiological parameter.

16. A rate responsive pacemaker comprising:

an A-mode ultrasound probe adapted for implantation in a right ventricle of a heart, said ultrasound probe emitting an ultrasound signal and receiving at least one echo of said ultrasound signal from at least one cardiac segment of the left ventricle;

a unit connected to said ultrasound probe for identifying a time difference between emission of said ultrasound signal and reception of said echo and, from said time difference, determining a position of said cardiac segment, said cardiac segment having a position which, at least when reflecting said ultrasound signal, is correlated to cardiac performance, and said unit deriving an indication of said cardiac performance from said position of said cardiac segment; and a pulse generator adapted to deliver stimulation pulses to said heart dependent on said cardiac performance.

17. A method for cardiac monitoring with an implantable device, comprising the steps of:

implanting an A-mode ultrasound probe in a right ventricle of a heart, and emitting an ultrasound signal from said probe toward a left ventricular wall, and receiving at least one echo of said ultrasound signal from said left ventricular wall;

identifying a time difference between emission of said ultrasound signal and reception of said echo and, from said time difference, determining a position of said left ventricular wall, said left ventricular wall having a position which, at least when reflecting said ultrasound signal, is correlated to cardiac performance; and deriving an indication of said cardiac performance from said position of said left ventricular wall.

18. A method as claimed in claim 17 wherein the step of emitting said ultrasound signal toward a left ventricular wall comprises emitting said ultrasound signal toward a medial portion of an endocardial wall of said left ventricle and a lateral portion of the endocardial wall of the left ventricle.

* * * * *